United States Patent
Hanson et al.

(10) Patent No.: US 9,949,755 B2
(45) Date of Patent: Apr. 24, 2018

(54) SURGICAL ACCESS SYSTEMS, INSTRUMENTS AND ACCESSORIES

(71) Applicant: ZIMMER KNEE CREATIONS, INC., Exton, PA (US)

(72) Inventors: Shaun B. Hanson, West Chester, PA (US); Christopher D. Mandeen, West Chester, PA (US)

(73) Assignee: ZIMMER KNEE CREATIONS, INC., Exton, PA (US)

( * ) Notice: Subject to any disclaimer, the term of this patent is extended or adjusted under 35 U.S.C. 154(b) by 136 days.

(21) Appl. No.: 13/854,796

(22) Filed: Apr. 1, 2013

(65) Prior Publication Data
US 2013/0261650 A1    Oct. 3, 2013

Related U.S. Application Data

(60) Provisional application No. 61/618,180, filed on Mar. 30, 2012.

(51) Int. Cl.
*A61B 17/34* (2006.01)
*A61B 17/88* (2006.01)
*A61B 17/00* (2006.01)

(52) U.S. Cl.
CPC ...... *A61B 17/3476* (2013.01); *A61B 17/3472* (2013.01); *A61B 17/8816* (2013.01);
(Continued)

(58) Field of Classification Search
CPC ............ A61B 17/3476; A61B 17/3472; A61B 17/8816; A61B 2017/00469; A61B 2017/00486; A61B 17/7097; A61B 17/8855; A61B 17/8805; A61B 17/1671; A61B 17/00234; A61B 17/32002; A61B 17/32053; A61B 17/1637; A61B 10/025;
(Continued)

(56) References Cited

U.S. PATENT DOCUMENTS

| 5,514,137 A | 5/1996 | Coutts |
| 5,556,429 A | 9/1996 | Felt |

(Continued)

FOREIGN PATENT DOCUMENTS

WO    WO-2013149256 A3    10/2013

OTHER PUBLICATIONS

Invitation to Pay Additional Fees for corresponding International Appl. No. PCT/US2013/034852 dated Jul. 2, 2013.
(Continued)

*Primary Examiner* — Jonathan Miles
*Assistant Examiner* — Mohamed Gabr
(74) *Attorney, Agent, or Firm* — Schwegman Lundberg & Woessner, P.A.

(57) ABSTRACT

The present disclosure provides a modular instrument system for accessing a site within a patient's body, such as for example, to inject or remove material. In one exemplary embodiment, an access device is coupled to an adapter and power drilled into a site within a patient. Once the access device is in position, the adapter may be further attached to other instruments, or to an injection or extraction system. The adapter may accommodate various other connectors to make the instrument system compatible with a variety of other surgical instruments and tools.

23 Claims, 17 Drawing Sheets

(52) U.S. Cl.
CPC ... *A61B 17/8819* (2013.01); *A61B 2017/00469* (2013.01); *A61B 2017/00486* (2013.01)

(58) Field of Classification Search
CPC .. A61B 2017/00734; A61B 2010/0258; A61B 2017/0046; A71B 2017/00486; A61F 2/4601; A61F 2002/4635
USPC ............ 606/92, 93, 94, 167, 170, 185; 604/93.01, 117, 164.01, 506, 21; 600/566
See application file for complete search history.

(56) References Cited

U.S. PATENT DOCUMENTS

| | | | |
|---|---|---|---|
| 5,755,809 A | 5/1998 | Cohen | |
| 6,140,452 A | 10/2000 | Felt | |
| 6,235,043 B1 | 5/2001 | Reiley | |
| 6,241,734 B1 | 6/2001 | Scribner | |
| 6,248,110 B1 | 6/2001 | Reiley | |
| 6,306,177 B1 | 10/2001 | Felt | |
| 6,312,394 B1 * | 11/2001 | Fleming, III | ........ A61B 10/025 600/567 |
| 6,395,007 B1 | 5/2002 | Bhatnager | |
| 6,554,778 B1 * | 4/2003 | Fleming, III | ................. 600/567 |
| 6,564,083 B2 | 5/2003 | Stevens | |
| 6,607,561 B2 | 8/2003 | Brannon | |
| 6,613,054 B2 | 9/2003 | Scribner | |
| 6,719,761 B1 | 4/2004 | Reiley | |
| 6,746,451 B2 | 6/2004 | Middleton | |
| 6,827,720 B2 | 12/2004 | Leali | |
| 6,863,899 B2 | 3/2005 | Koblish | |
| 6,887,246 B2 | 5/2005 | Bhatnager | |
| 7,153,307 B2 | 12/2006 | Scribner | |
| 7,261,720 B2 | 8/2007 | Stevens | |
| 7,708,742 B2 | 5/2010 | Scribner | |
| 7,771,431 B2 | 8/2010 | Scribner | |
| 7,811,290 B2 | 10/2010 | Rabiner | |
| 8,152,813 B2 | 4/2012 | Osorio | |
| 8,168,692 B2 | 5/2012 | Wenz | |
| 2003/0138473 A1 | 7/2003 | Koblish | |
| 2004/0019330 A1 * | 1/2004 | Ashby | ................. A61B 17/0057 604/168.01 |
| 2005/0090852 A1 | 4/2005 | Layne et al. | |
| 2005/0119219 A1 | 6/2005 | Bellini | |
| 2006/0064164 A1 | 3/2006 | Theien | |
| 2008/0045857 A1 * | 2/2008 | Miller et al. | ................. 600/566 |
| 2008/0287859 A1 * | 11/2008 | Miller et al. | ................... 604/21 |
| 2010/0076503 A1 | 3/2010 | Beyar | |
| 2010/0179549 A1 | 7/2010 | Keller | |
| 2010/0298836 A1 * | 11/2010 | Jordan | ............................ 606/94 |
| 2012/0059380 A1 | 3/2012 | Deangelo et al. | |

OTHER PUBLICATIONS

May 12, 2008 Riddle Memorial Hospital, Medial, PA 19063 Operative Report. Surgeon: Peter F Sharkey, M.D.; Right knee, medial tibial plateau; A cannulated bone biopsy needle was placed into the bone under fluoroscopic guidance; Implant used: Stryker Orthopedics Hydroset (Bone Substitute Material); Surgeon also expressed difficulty in injecting the bone substitute.

Oct. 27, 2008 SPU Operative Report. Surgeon: Steven B Cohen, M.D.; An Anterior Cruciate Ligament (ACL) portal-creation device was repurposed for this surgery; The tibial probe was placed on the medial femoral condyle, with the tunnel guide secured proximally on the thigh; The surgeon expressed difficulty in positioning and stabilizing the guide; A cannulated pin was placed through the tunnel guide and placed distally into the medial femoral condyle; No implant was injected into the bone.

Nov. 10, 2008 SPU Operative Report. Surgeon: Steven B Cohen, M.D.; Treatment of the central medial tibial plateau; A guide pin was inserted into the medial tibial plateau; An endo button drill bit was used to expand the drill hole; One cubic centimeter (cc) of cement was inserted into the bone; A second drill hole was made from below, and a second cc was inserted into the bone.

"International Application Serial No. PCT/US2013/034852, International Search Report dated Sep. 27, 2013", 6 pgs.

* cited by examiner

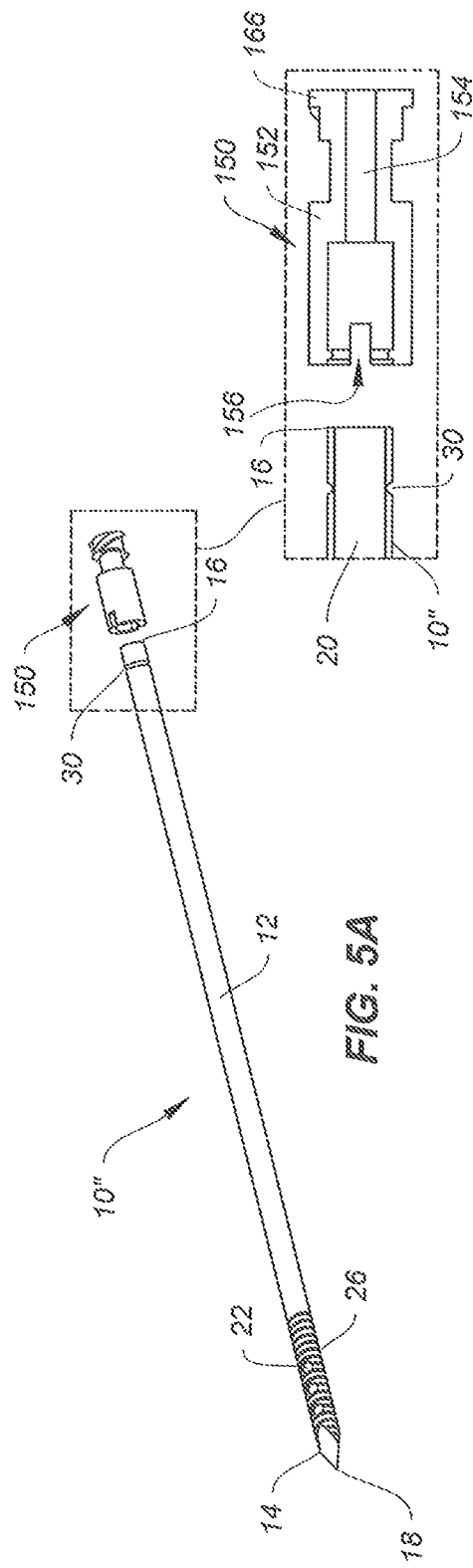
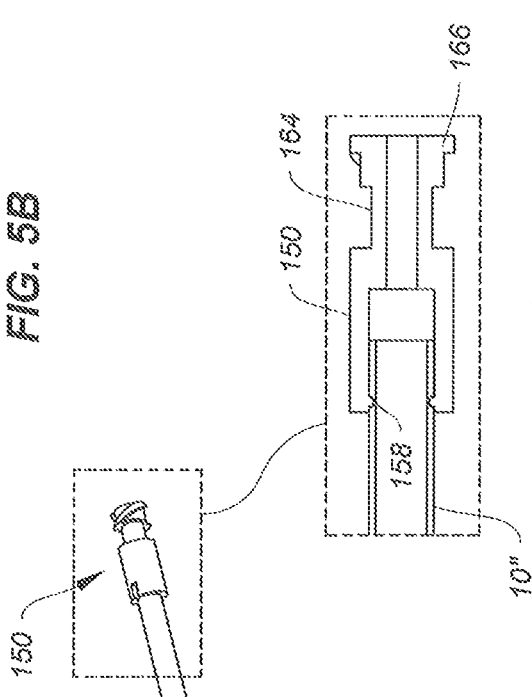
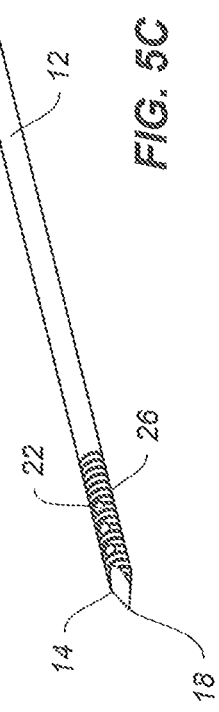
FIG. 5A
FIG. 5B
FIG. 5C
FIG. 5D

SURGICAL ACCESS SYSTEMS, INSTRUMENTS AND ACCESSORIES

CROSS-REFERENCE TO RELATED APPLICATIONS

This application claims priority to U.S. Provisional No. 61/618,180 filed Mar. 30, 2012 and entitled "Surgical Access Systems, Instruments and Accessories," the content of which is incorporated by reference in its entirety.

FIELD

The present disclosure relates to medical instruments and accessories, and more particularly, to surgical access systems, instruments and accessories for the injection or extraction of materials into or out of a patient's body. Even more particularly, these access systems, instruments and accessories can cooperate with other known surgical instruments, including power tools, for driving such systems, instruments and accessories directly into the patient's body.

BACKGROUND

Many medical procedures or treatments require internal access into the patient's body. Surgical access into the body may sometimes involve a working channel for the insertion of tools for the injection or removal of materials into or out of a desired site within the body. In a majority of cases, an access device, such as a cannula, is used to provide this working channel. For example, in many surgical bone treatments, a portal to inject directly into the bone is employed. This portal is conventionally created with a standard trocar and cannula. Generally, after removing the trocar, the surgeon will manually drive, either by pushing, twisting, or a combination of both, the cannula into the bone. The residing cannula provides a clear path into the bone for effecting treatment.

Problems arise, however, when the cannula must overcome a large resistive force as it is being inserted and plunges too far forward. Another problem is created during bone treatments when the step of manually twisting the cannula into bone creates an oval cavity in the cortical bone, negating any seal between the cannula and bone. These issues can lead to damage of cancellous/cortical bone, or an incomplete fill with extravasations.

It would therefore be desirable to provide the necessary tools and instruments to allow a powered tool to drive an access device such as a cannula, pin, needle, or other known injection or extraction portal, directly into the patient's body. It would also be desirable to provide surgical access instruments and systems that allow the surgeon with more control to create the working channel for medical treatments. It would be even more desirable to provide these instruments and systems with better depth control, alignment control, and ease of use.

SUMMARY

The present disclosure provides embodiments for surgical access to a site within a body of a patient. More particularly, the present disclosure provides systems, instruments and accessories that allow an access device, such as a cannula, pin, needle, or other known injection or extraction portal, to be power driven directly into the patient.

In one exemplary embodiment, an instrument system may comprise an access device that is cannulated and one or more adapters that can be interchangeably attached to the access device. The adapters allow the access device to be able to accommodate various connectors to another system. In one embodiment, an adapter is configured to provide a Luer lock. In another embodiment, an adapter is configured to provide a Hudson connector. These adapters serve as a connection bridge, allowing the access device to engage other surgical instruments or medical systems.

In another exemplary embodiment, an instrument system for providing access to a site within a body of a patient is provided. The system can comprise a cannulated access device having a first leading end, a second trailing end and an elongate shaft extending therebetween. The access device may comprise at least one fenestration. Also, the access device may comprise at least one visual marking such as etchings, colored bands, radiopaque labels, or other markers along the length of the shaft. In some embodiments, the access device may have a first leading end that is open.

The system can also include an adapter configured to attach to the second trailing end of the access device and enable the access device to engage a separate component, such as a connector for a drill instrument or an extraction/injection system. The adapter may comprise a main body, a central opening within the main body for receiving a portion of the second trailing end of the access device, and a connector end. In one exemplary embodiment, the separate component may comprise a connector configured to mate with the adapter and provide a connection to another instrument or system, such as for example a drill, injector, or extraction instrument.

The first leading end of the access device may include threads. The first leading end of the access device may have a sharp tip. Also, the second leading end of the access device may include threads. The adapter may be configured to attach to the second trailing end by a threaded connection. Alternatively, the adapter may be configured to attach to the second trailing end by other connection means, such as a friction fit, an interference fit, or a snap fit, for example. In some embodiments, the adapter may comprise a central stem configured for insertion through the central opening of the access device. The central stem may have a sharp distal tip, and may be configured to extend through an open leading end of the access device.

In still another exemplary embodiment, the adapter may comprise a clamp configured to provide a press-fit connection with the second trailing end of the access device. The clamp may comprise a C-ring, and may also include a tightening screw in one embodiment. In another embodiment, the C-ring may include a cam lever. In still another embodiment, the C-ring may comprise a plurality of flanges that may be separated by slots. These flanges may be threaded as well. The flanges may be secured onto the second trailing end of the access device with a threaded washer.

The system may further comprise a drill instrument having a main body with a slot for receiving the shaft of the access device, a handle, and a trigger for actuating the drill instrument. This drill instrument may be powered to enable fast and accurate insertion of the access device with little effort. The drill instrument may allow the access device to be driven into the access site in a straight path. In addition, the receiving slot of the main body allows the drill instrument to be removed from the access device after it has been driven into the patient with little disturbance. For example, the drill instrument may be removed from the access device by pulling down and away from the access device, releasing the access device from the drill instrument via the receiving slot, and without the need to go over the second trailing end of the access device.

In one exemplary embodiment, the drill instrument may comprise a catch mechanism including a plurality of driver discs. The drill instrument may further comprise a gear mechanism including a main gear, at least one secondary gear, a motor for driving the gears, and at least one spring biasing the gears against the motor. The drill instrument may further comprise a release mechanism including a release button extending from a shaft in connection with the main gear.

It is to be understood that both the general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIG. 5A shows an exploded view of an exemplary access device and adapter in accordance with even still another embodiment of the present disclosure.

FIG. 5B shows an enlarged detailed view of a part of the access device and adapter shown in FIG. 5A.

FIG. 5C shows another view of an exemplary access device and adapter shown in FIG. 5A.

FIG. 5D shows an enlarged detailed view of a part of the access device and adapter shown in FIG. 5C.

The foregoing and other features of the present disclosure will become apparent to one skilled in the art to which the present disclosure relates upon consideration of the following description of exemplary embodiments with reference to the accompanying drawings.

DESCRIPTION OF THE EMBODIMENTS

The present disclosure provides a modular instrument system for accessing a site within a patient's body, such as for example, to inject or remove material. The embodiments include systems, instruments and accessories that allow an access device, such as a cannula, pin, needle, or other known injection or extraction portal, to be power driven directly into the patient. The ability to drive an access device or portal directly into the patient's body using power such as with a standard power drill enables the user to gain better control of the process, such as by reducing the chances of misalignment during insertion, and over-insertion or under-insertion, to name a few examples.

In one exemplary embodiment, an access device is drilled into the access site within a patient, for example, using a standard wire driver. Once the access device is in place, an adapter may be attached to the access device to adapt it to an injection and/or extraction system, such as a standard syringe or Luer lock that may be connected to a standard power tool. The adapter may accommodate various connectors to make the instrument system compatible with a variety of known surgical instruments and tools.

In an effort to give the surgeons more control, the embodiments provide an access device that can be drilled into a patient's body with better control of depth because no excessive force is needed, and furthermore can be driven into the patient in a straight path. Once the device is in place, the access device can serve as a port for injection or withdrawal of materials from the patient's body. This disclosure describes embodiments by which to drive in an access device using a power tool in a controlled manner, while allowing for a way to connect the access device to another system, such as an injection or extraction system.

Reference will now be made to the figures to illustrate various aspects and embodiments of the present disclosure. In the following detailed description, numerous specific details are set forth to provide a full understanding of the present disclosure. It will be apparent, however, to one ordinarily skilled in the art that the present disclosure may be practiced without some of these specific details. In other instances, well-known structures and techniques have not been shown in detail to avoid unnecessarily obscuring the present disclosure.

Figure 1A:
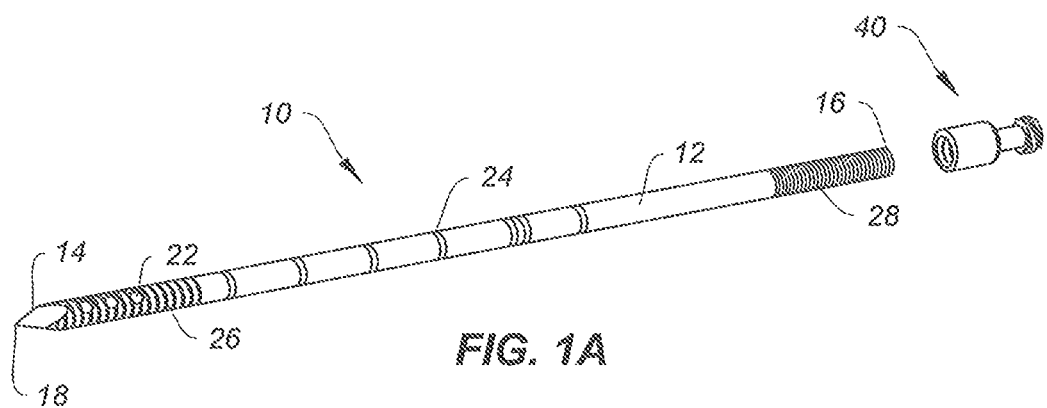
FIG. 1A shows an exemplary access device and adapter in accordance with an embodiment of the present invention.
Figure 1B:
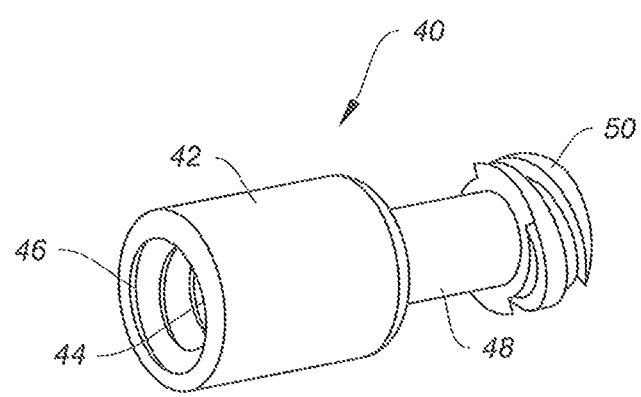
FIG. 1B shows an enlarged view of the adapter shown in FIG. 1A.
Figure 1C:
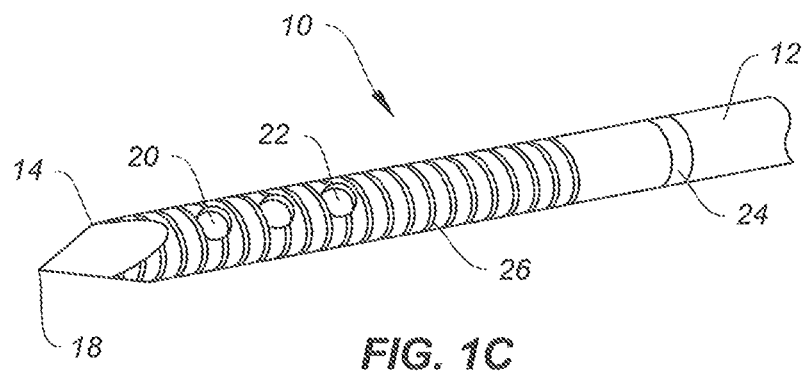
FIG. 1C shows an enlarged view of a portion of the access device shown in FIG. 1A.

FIGS. 1A-1C show an exemplary access device and adapter in accordance with an embodiment of the present disclosure. As shown, an access device 10 may comprise a shaft 12, a first leading end 14, a second trailing end 16, a tip 18, a central channel 20, fenestrations 22, and etchings 24. In this embodiment, the first leading end 14 may comprise threads 26. Threads 26 may be provided to help anchor the access device 10 into bone tissue such as during a bone treatment procedure. These threads 26 may also facilitate insertion and distraction of the access device 10 into or out of the patient. For instance, the threads 26 may help to draw the access device 10 towards the target area of insertion as it is driven into the patient, similar to a pulling action. Likewise, the threads 26 may also help draw the access device 10 away from the target area as it is removed from the patient, similar to a pushing action. Other surface features, such as surface roughenings, barbs, teeth, projections, or spikes may also be used in the embodiments. Of course, it is understood that these threads 26 may be an optional feature of the access device 10 and other embodiments may omit the threads 26 from the access device 10 without detriment to its overall function or usefulness.

The second trailing end 16 may also comprise threads 28. Threads 28 are configured to allow a threaded connection to an adapter 40. Alternative connection means, such as a friction fit, an interference fit, a snap fit, etc., may be employed in the embodiments.

FIG. 1B shows an enlarged view of the adapter shown in FIG. 1A. In particular, the adapter 40 may comprise sleeve or main body 42 having a central opening 44, internal threads 46, and a shaft 48 terminating into a connector end 50.

The central opening 44 and internal threads 46 connect the adapter 40 to the access device 10. The adapter 40 may bridge to another system, such as an extraction or injection system. As shown, the connector end 50 may be threaded in one embodiment to connect the adapter 40 to another system. For example, the connector end 50 may be configured to attach to a Luer lock for a syringe. Alternatively, the connector end 50 may comprise connection means, such as a friction fit, an interference fit, a snap fit, etc. The adapter 40 may serve to connect an access device 10 to an instrument such as a power tool for driving the access device 10 directly into the patient's body. Presently, these types of Luer lock or other connection end adapters are provided as a unitary body with the access device. Applicants have discovered a system for providing separable and connectable adapters with access devices that allow the combination to be power driven into a patient's body. This system thus allows the user to remove the adapter once the access device is inserted, without disturbing the rest of the access device.

FIG. 1C shows an enlarged view of a portion of the access device 10 shown in FIG. 1A. In particular, an enlarged view of the first leading end 14 of the access device is shown. As shown, the first leading end 14 may terminate into a sharpened tip 18 to make it suitable for piercing bone or other tissue.

As also shown, the access device may comprise a plurality of fenestrations 22 in proximity to the first leading end 14. In FIGS. 1A and 1C, three fenestrations 22 are shown; however, it is understood that the access device 10 may comprise any number of fenestrations.

Etchings 24 may be provided at various positions along the length of the shaft 12. These etchings 24 may be marked in various fashions, such as with colors or with graphics, to make them visible during use. In addition, the etchings 24 may comprise radiopaque material to make them identifiable under fluoroscopy or X-ray intra-operatively.

Figure 2A:
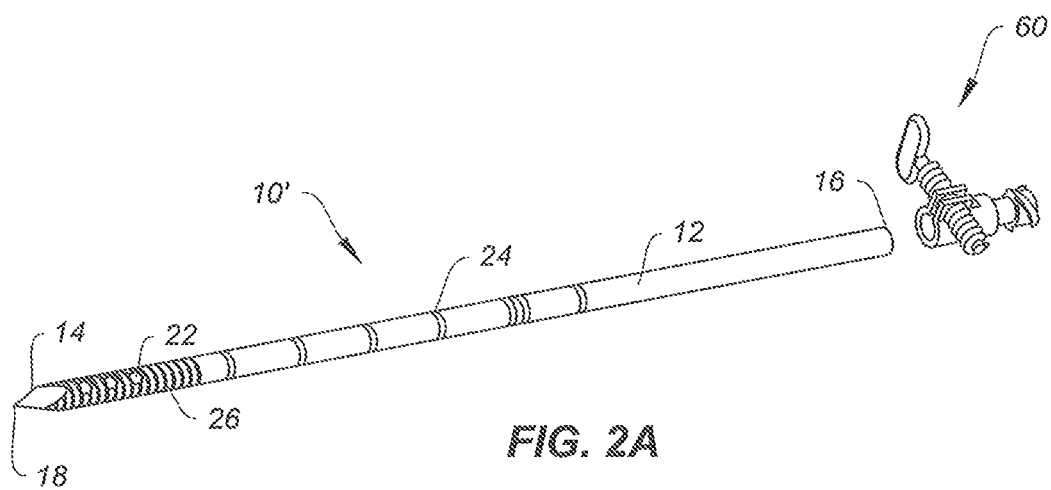
FIG. 2A shows an exemplary access device and adapter in accordance with another embodiment of the present disclosure.

FIG. 2A shows an exemplary access device and adapter in accordance with another embodiment of the present disclosure. In this embodiment, the access device 10' is similar to the access device 10 shown in FIGS. 1A-1C. However, as shown, the access device 10' may lack threads at second trailing end 16.

Instead, an adapter 60 may be fitted over second trailing end 16 and retained via a friction fit. For example, the adapter 60 may be a conventional Luer lock with a C-ring sleeve.

Figure 2B:
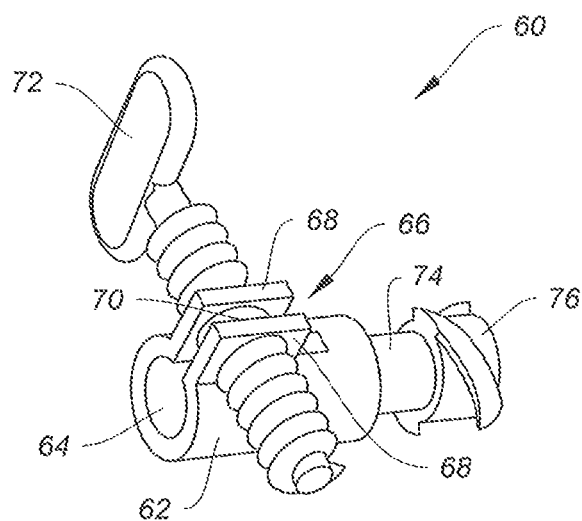
FIG. 2B shows an enlarged view of the adapter shown in FIG. 2A.

FIG. 2B shows an enlarged view of the adapter 60 shown in FIG. 2A. The adapter 60 may comprise a main body 62, a central opening 64, a slit 66, a pair of tabs 68 having threaded holes 70, a tightening screw 72, and a shaft 74 terminating into a connector end 76. The adapter 60 may be slid over the second trailing end 16 and clamped on to access device 10' using tightening screw 72. The adapter 60 may also comprise rubber washers, O-rings, gaskets, sealing rings, and the like to provide a sealed connection.

Figure 3A:
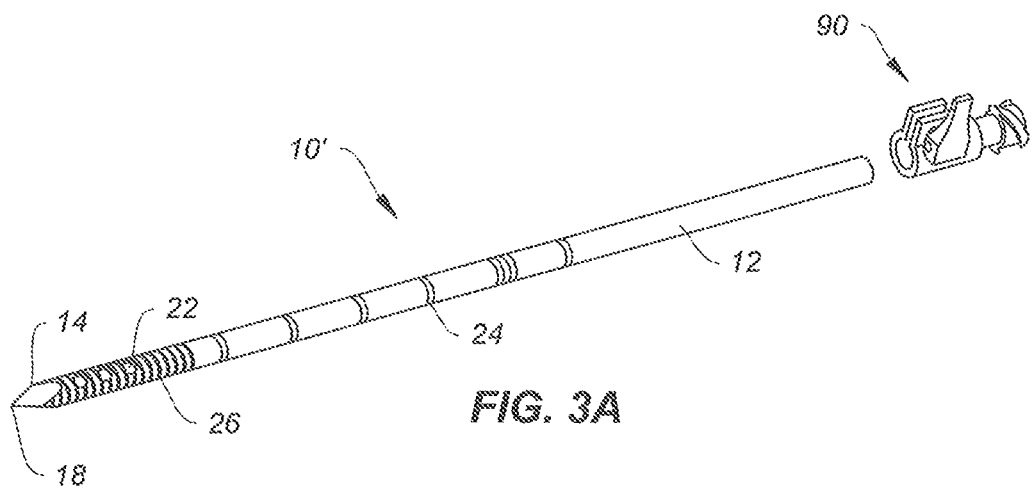
FIG. 3A shows an exemplary access device and adapter in accordance with yet another embodiment of the present disclosure.

FIG. 3A shows an exemplary access device and adapter in accordance with yet another embodiment of the present disclosure. In this embodiment, the access device 10' is similar to the access device 10' shown in FIGS. 2A and 2B, but with a different adapter 90. In this embodiment, the adapter 90 is again fitted over second trailing end 16 and retained via a C-ring held in place by a cam lever 100.

Figure 3B:
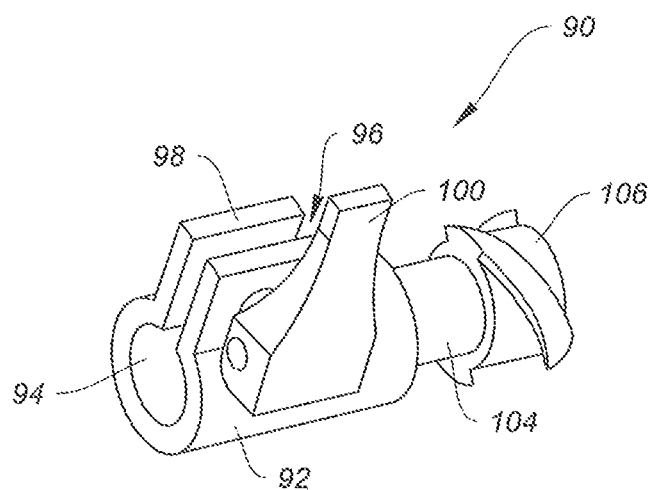
FIG. 3B shows an enlarged view of the adapter shown in FIG. 3A.

FIG. 3B shows an enlarged view of an adapter 90 shown in FIG. 3A. As shown, the adapter 90 is similar to adapter 60 of FIG. 2B. The adapter 90 may comprise a main body 92, a central opening 94, a slit 96, a pair of tabs 98, a cam lever 100, and a shaft 104 terminating into a connector end 106. The adapter 90 may be slid over the second trailing end 16 and clamped on to access device 10' by engaging cam lever 100. The adapter 90 may also comprise rubber washers, O-rings, gaskets, sealing rings, and the like to provide a sealed connection.

Figure 4A:
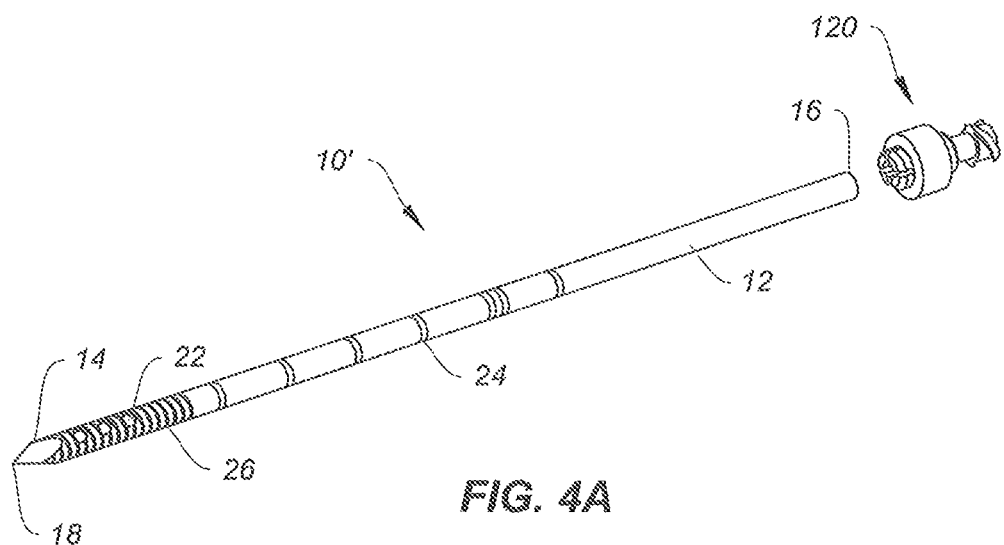
FIG. 4A shows an exemplary access device and adapter in accordance with still another embodiment of the present disclosure.

FIG. 4A shows an exemplary access device and an adapter 120 in accordance with yet another embodiment of the present disclosure. As shown, the adapter 120 shares similar features to adapters 60, 90. The adapter 120 may comprise a main body 122, a central opening 124, flanges 126 having threads 130 separated by slits 128, and a shaft 134 terminating into a connector end 136.

Similar to adapters 60, 90, the adapter 120 may be slid over the second trailing end 16 and tightened. In particular, the main body 122 may be configured as a threaded washer, and upon rotation, tightens flanges 126 around the second trailing end 16 of the access device 10'. This configuration enables a sealed connection for injection of material without overflow. The adapter 120 may also comprise rubber washers, O-rings, gaskets, sealing rings, and the like to provide a sealed connection.

Figure 4B:
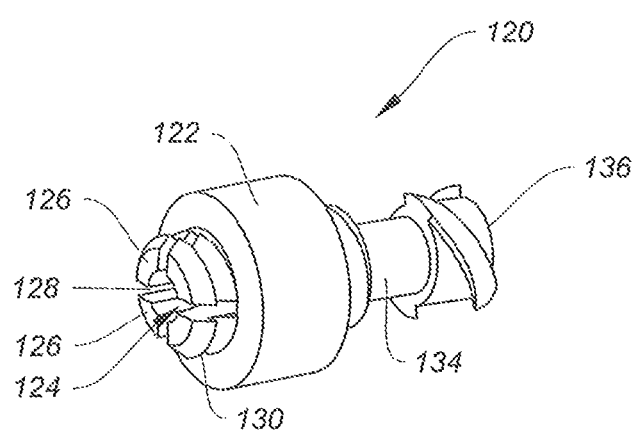
FIG. 4B shows an enlarged view of the adapter shown in FIG. 4A.

FIG. 4B shows an enlarged view of the adapter 120 shown in FIG. 4A. The adapter 120 may comprise a connector end 136 that may be configured to connect to a conventional Luer lock for a syringe.

FIG. 5A shows an exploded view of an exemplary access device 10" and adapter 150 in accordance with yet another embodiment of the present disclosure. In this embodiment, the access device 10" is similar to the access device 10' shown in FIGS. 2A-4B, but access device 10" may further comprise a groove 30 near second trailing end 16. In this embodiment, an adapter 150 may be configured to snap-fit onto the access device 10" by engaging the groove 30.

FIG. 5B shows an enlarged detailed view of a part of the access device 10" and the adapter 150 shown in FIG. 5A. As shown, the adapter 150 may comprise a main body 152, a central opening 154, cutouts 156, one or more internal notches 158, and a shaft 164 terminating into a connector end 166.

FIG. 5C shows another view of an exemplary access device and adapter shown in FIG. 5A. FIG. 5D shows an enlarged detailed view of a part of the access device and adapter shown in FIG. 5C. In particular, FIGS. 5C and 5D show how adapter 150 may be connected to the access device 10". In this embodiment, the adapter 150 has a contour or geometry that matches access device 10" and allows for a detachable snap-fit mechanism. Alternatively, the adapter 150 may employ a slip-fit to engage the access device 10".

As described, the embodiments provide an instrument system that is modular. For example, once an adapter has been attached to an access device, an instrument connector for various other surgical or medical instruments may be secured on to the adapter. This feature allows the embodiments to interchangeably work with different instruments, such as insertion tools, extraction and injection systems, distraction tools, etc. FIGS. 6A-8C are provided to illustrate various secondary connectors that may be used with the embodiments.

Figure 6A:
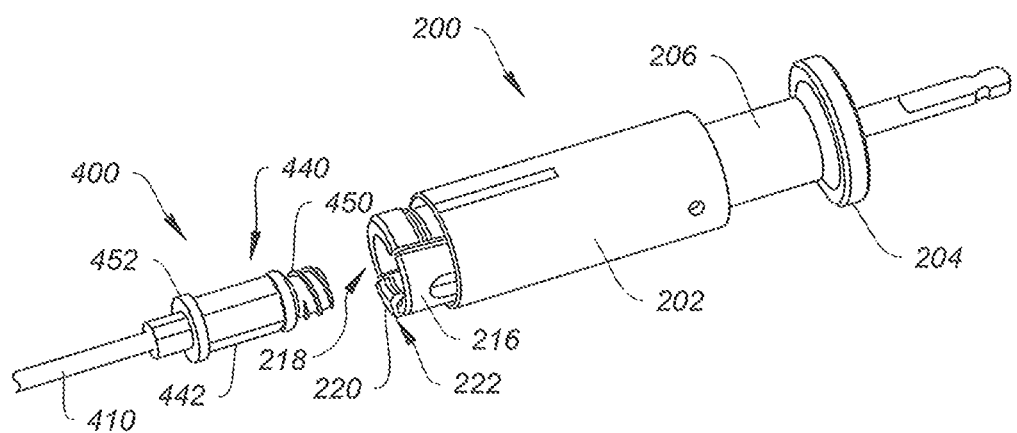
FIG. 6A shows an exemplary connector that may be coupled to the adapter of FIG. 5A.

In the example shown in FIGS. 6A-6E, a connector 200 allows connection to the access device with a Luer lock and drilling into site of a patient's body with a power instrument. FIG. 6A shows an exemplary connector 200 that may be coupled to a combined access device and adapter 400. The combined access device and adapter 400 share similar features to the access device 10 and adapter 40 of FIGS. 1A and 1B, with like features sharing the same reference numeral following the prefix "4". The adapter component 440 of the combined access device and adapter 400 may comprise a main body 442 having a connector end 450 configured for attachment to an instrument such as a power tool (not shown). The main body 442 and connector end 450 may be separated by a flange 452 that enables the adapter component 440 to be coupled with a connector, as will be described in more detail below.

In this embodiment, the adapter component 440 may be overmolded onto the access device component 410 with a geometry that enables mating with the connector 200. The geometry of the adapter 440 may mirror an internal geometry of the connector 200 to allow for the application of force to rotate and position the access device 410. As shown and described, the combined access device and adapter 400 are an integral unit; the adapter component 440 may be molded onto the access device component 410. Of course, it is understood that these components may be provided separately, and configured for attachment such as with a threaded connection, press-fit connection, interference fit connection, snap-fit, etc. as in previously described and illustrated embodiments. However, when desired, these two components may be provided as a single unit, as shown and described here in FIGS. 6A-6E.

The connector 200 may comprise an outer shell 202 having a flanged end 204 and a neck 206. Internally, the connector 202 may comprise bumpers 208, 210, an inner shell 216 having a central opening 218, and flanges or legs 220 separated by slots 222. The flanges or legs 220 may also comprise internal notches 224.

The connector 200 may employ a plunger system 230 comprising a shaft 232 attached to the inner shell 216 and aligned by bumpers 208, 210. A housing 234 encloses a spring bias mechanism 236 exerting resistance against a flange 238. A notch 240 is provided on the terminal end of shaft 232.

Figure 6B:
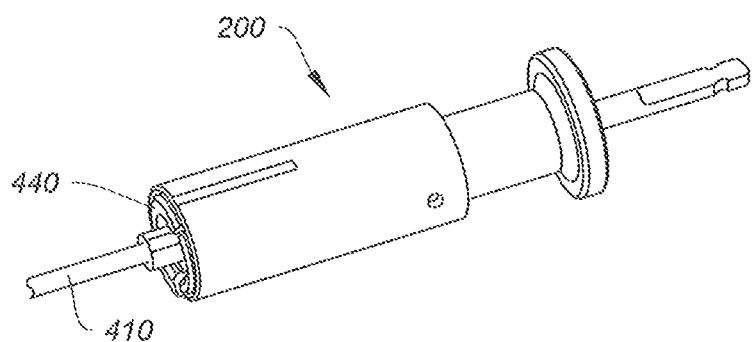
FIG. 6B shows another view of the connector of FIG. 6A attached to the adapter of FIG. 5A.
Figure 6C:
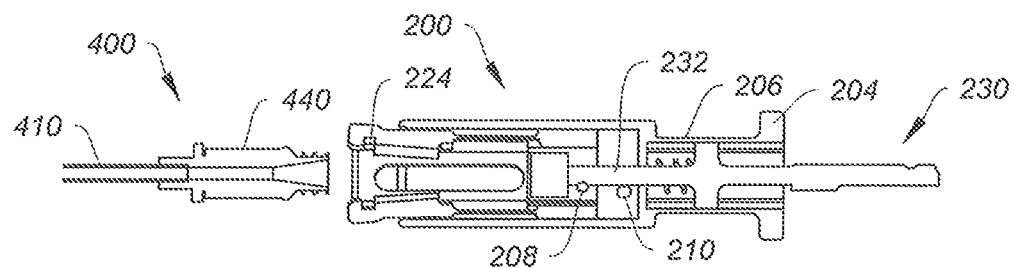
FIG. 6C shows an exploded, cross-sectional view of the connector of FIG. 6A.
Figure 6D:
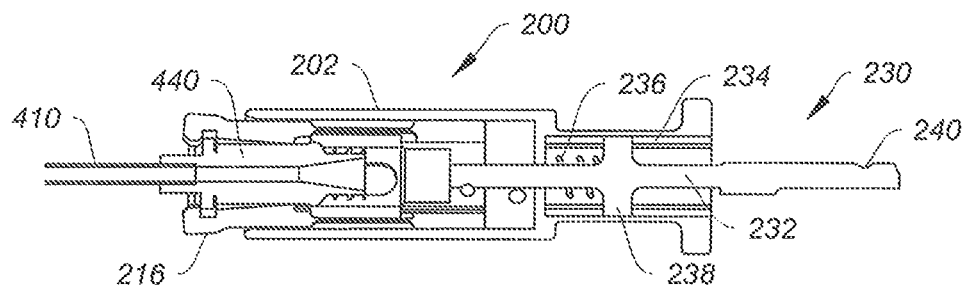
FIG. 6D shows a cross-sectional view of the connector attached to the adapter.
Figure 6E:
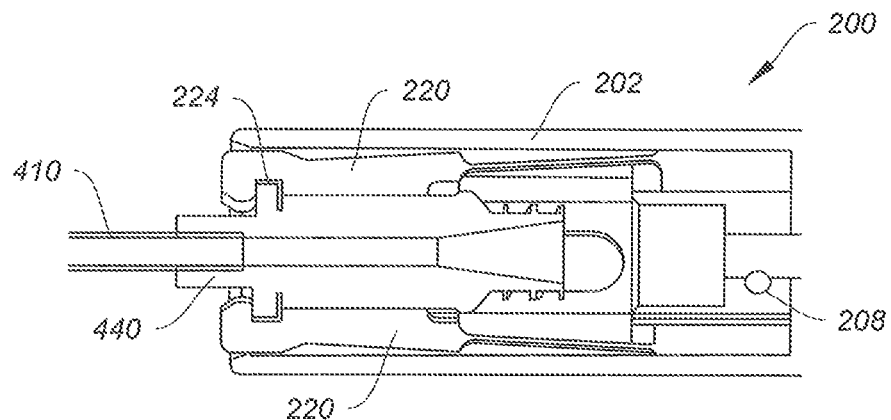
FIG. 6E shows an enlarged detailed view of a part of the connector shown in FIG. 6D.

In this embodiment, the connector 200 operates by retracting the outer shell 202 to allow the inner shell 216 to fit over the adapter component 440, as shown in FIG. 6C. When released, the outer shell 202 slides over the inner shell 216 and causes it to engage the molded geometry of the adapter component 440, and particularly the flange 452, as shown in FIGS. 6B, 6D, and 6E.

Furthermore, the terminal end of the shaft 232 can be attached to another instrument. For example, the terminal end of the shaft 232 may be shaped and include notch 240 to provide an AO connection or Hudson connection, etc. This form of connection provides a secure engagement to an instrument, such as a power tool, and allows for powered transmittal of torque in translation to the access device component 410. Alternatively, the connector 200 may comprise a wire extending from the outer shell 202.

Figure 7A:
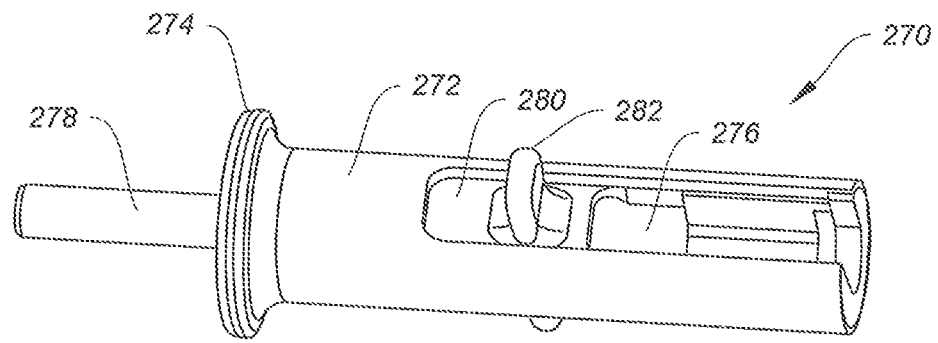
FIG. 7A shows another exemplary connector that may be coupled to an adapter.
Figure 7B:
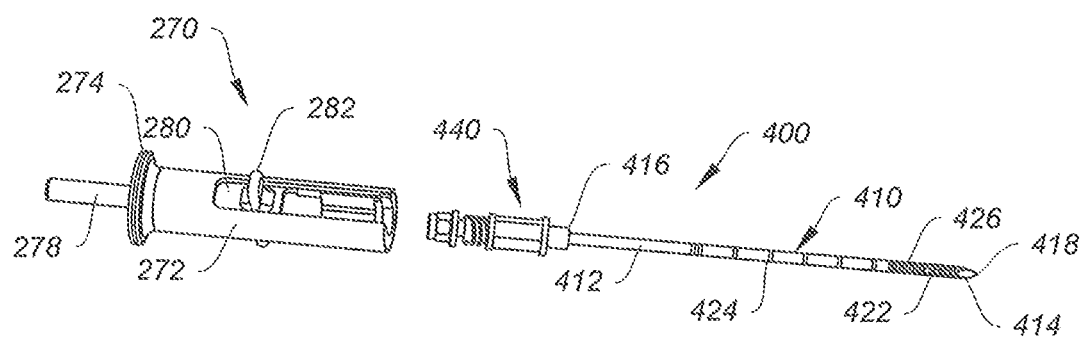
FIG. 7B shows an exploded view of the connector of FIG. 7A and combined adapter and access device.
Figure 7C:
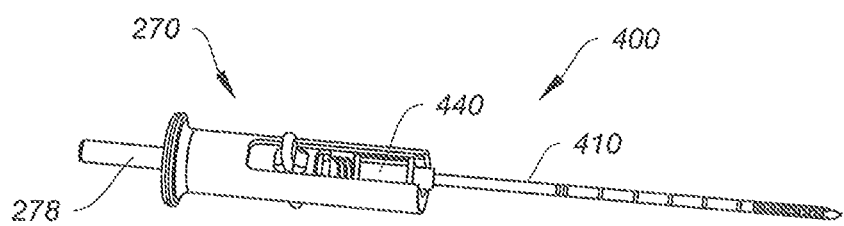
FIG. 7C shows the connector of FIG. 7A attached to the combined adapter and access device.

FIG. 7A shows another exemplary embodiment of a connector 270 that may be coupled to the combined access device and adapter 400. The combined access device and adapter 400 share similar features to the access device 10 and adapter 40 of FIGS. 1A and 1B, with like features sharing the same reference numeral following the prefix "4". The access device component 410 of the combined access device and adapter 400 may comprise a shaft 412, a first leading end 414, a second trailing end 416, a tip 418, a central channel 420, fenestrations 422, and etchings 424. In this embodiment, the first leading end 414 may comprise threads 426. As shown, the connector 270 may comprise an outer shell 272 having a flange 274, a slot 276, a stem 278, and an inner shell 280 having tabs 282. In this exemplary embodiment, the adapter component 440 may again be molded with a geometry that enables mating with the connector 270. The geometry of the adapter component 440 may mirror an internal geometry of the inner shell 280. FIG. 7B shows an exploded view of the connector of FIG. 8A and adapter and access device.

As shown in FIGS. 7A and 7B, the internal shell 280 can be retracted to allow the adapter component 440 of the combined access device and adapter 400 to be placed inside of the connector 270. Upon release, the internal shell 280 slides forward and engages the adapter component 440, as show in FIG. 7C. In similar fashion to adapters 200, 250, the stem 278 allows the connector 270 to be used with other various instruments, such as a power tool like an AO drill or an instrument having a Hudson connection, etc.

Figure 8A:
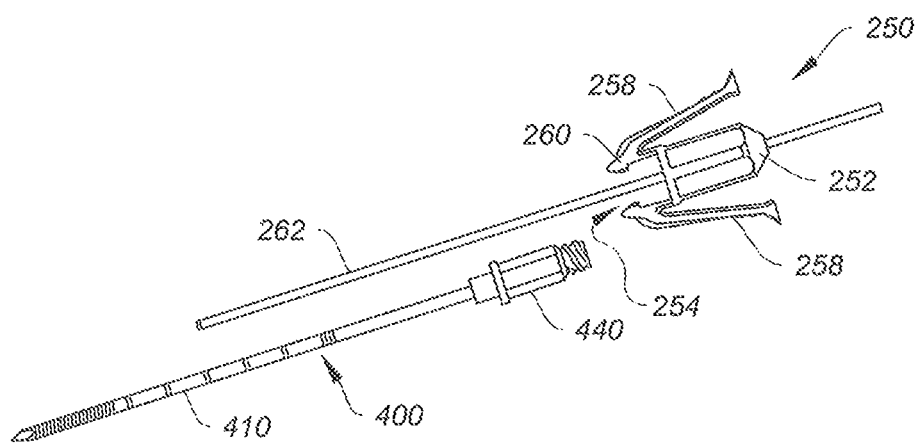
FIG. 8A shows another exemplary connector that may be coupled to a combined adapter and access device.
Figure 8B:
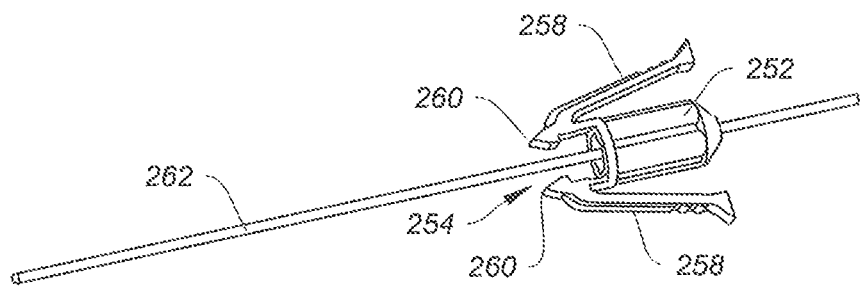
FIG. 8B shows a perspective view of the connector shown in FIG. 8A.

FIG. 8A shows another exemplary connector that may be coupled to the combined access device and adapter. In this embodiment, the adapter component 440 may again be molded with a geometry that enables mating with the connector 250. The geometry of the adapter component 440 may mirror an internal geometry of the connector 250 to allow for the application of force to rotate and position the access device component 410. The connector 250 may comprise a main body or cap 252, a central opening 254, a pair of wings 258 having notched ends 260, and a central stem 262 provided through the main body 252. FIG. 8B shows a perspective view of the connector 250 shown in FIG. 8A.

Figure 8C:
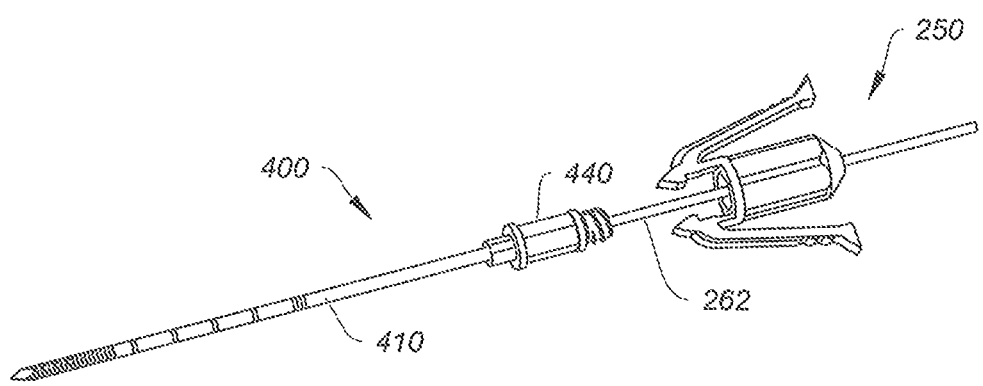
FIG. 8C shows the connector of FIG. 8A partially inserted into the combined adapter and access device.
Figure 8D:
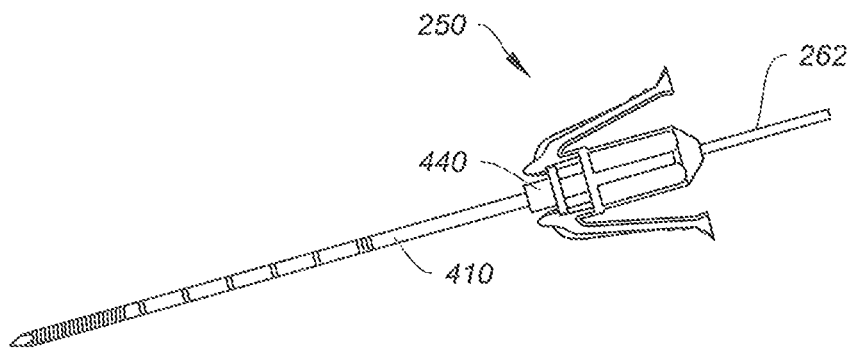
FIG. 8D shows the connector of FIG. 8A fully inserted into the combined adapter and access device.

FIG. 8C shows the connector of FIG. 8A partially inserted into the combined access device and adapter 400. FIG. 8D shows the connector of FIG. 8A fully inserted into the combined access device and adapter 400. During use, the stem 262 may be inserted through the connector 250 and into the central channel 420 of the access device component 410. The stem 262 may align the connector 250 over the adapter component 440. The connector 250 may then be slid over the stem 262 and placed over the overmolded adapter component 440. Once fully over the adapter component 440, the notched ends 260 may snap in place, and grab onto the adapter component 440, as shown in FIG. 8D. The notched ends 260 may be unsnapped by pressing the wings 258 inward towards the main body 252, releasing the notched ends 260 from its snapped-on position. In this embodiment, the adapter component 440 is shown providing a Luer lock. When attached, the connector 250 can twist, push, and pull the access device component 410 while preserving the Luer Lock. The connector 250 may be removed to allow use of the Luer lock on adapter 40.

Figure 9A:
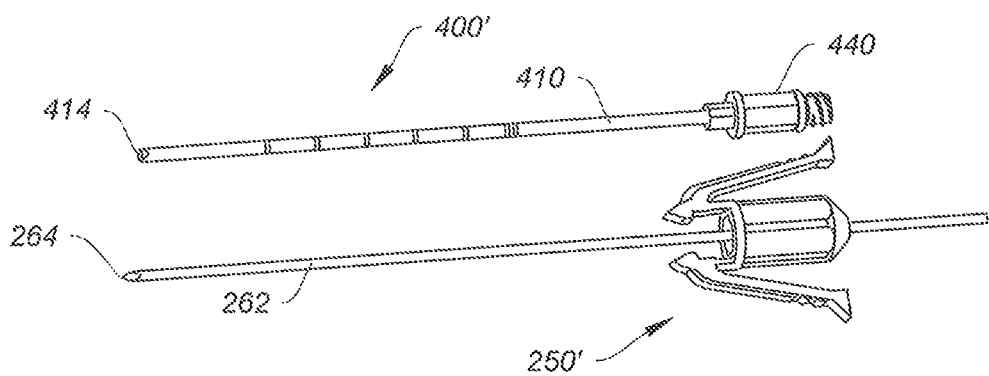
FIG. 9A shows an exploded view of still another exemplary connector that may be coupled to a combined adapter and access device.

FIG. 9A shows an exploded view of still another exemplary connector 250' that may be coupled to a combined adapter and access device 400'. The combined access device and adapter 400' share similar features to the combined access device and adapter 400 shown and described in FIG. 6A through FIG. 8D, with like features being designated by the same reference numerals. Accordingly, the access device component 410 of the combined access device and adapter 400' may also comprise a shaft 412, a first leading end 414, a second trailing end 416, and etchings 424. However, in this embodiment, the combined access device and adapter 400' includes an access device component 410 having a first leading end 414 that is open.

The connector 250' shares similar features to the connector 250 shown and described in FIGS. 8A-8D, with like features being designated by the same reference numerals. Accordingly, the connector 250' may also comprise a main body or cap 252, a central opening 254, a pair of wings 258 having notched ends 260, and a central stem 262 provided through the main body 252. However, in this embodiment, the central stem 262 terminates into a sharp tip 264.

Figure 9B:
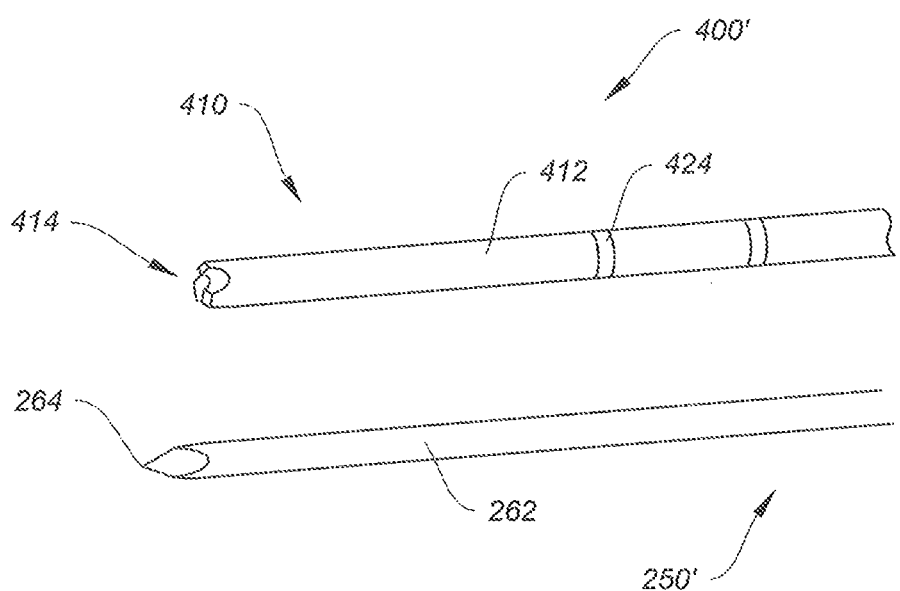
FIG. 9B shows an enlarged detailed view of a part of the connector and access device shown in FIG. 9A.

As shown in detail in FIG. 9B, the shaft 412 of the access device component 410 may terminate in a first leading end 414 that is open. This open end 414 allows the sharp tip 264 of the central stem 262 of the connector 250' to extend through, thereby creating a sharp tip for entry of the combined devices into the patient. If so desired, the open end 414 may also be shaped so as to have sharp edges or projections for more secure engagement such as to bone tissue.

Figure 10A:
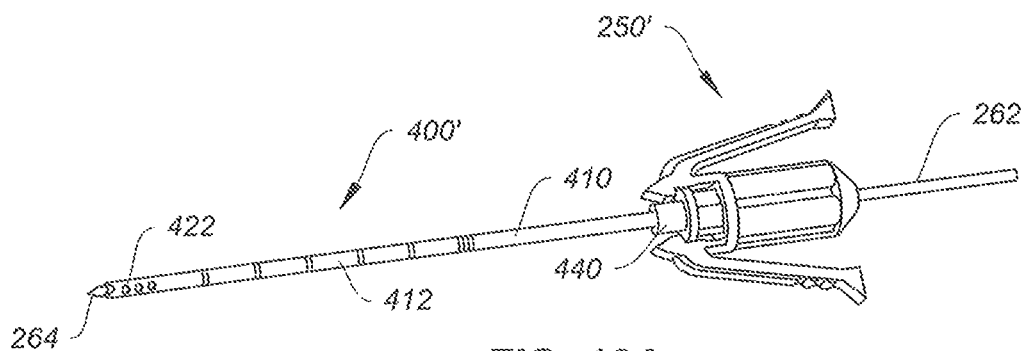
FIG. 10A shows yet another exemplary connector and combined access device and adapter in accordance with an embodiment of the present disclosure.
Figure 10B:
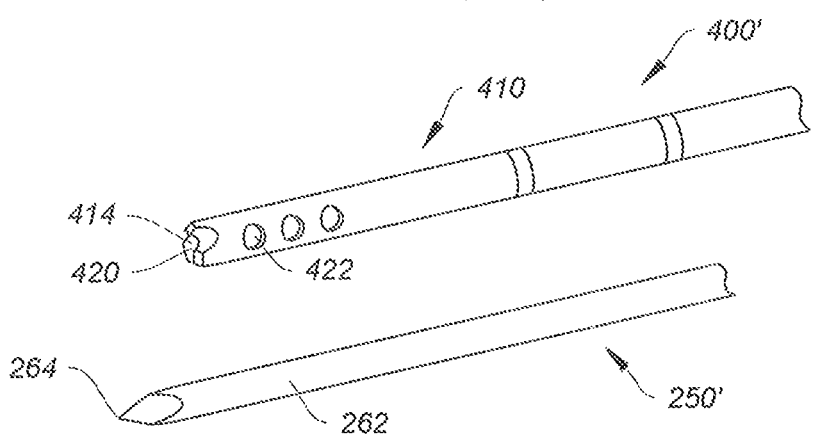
FIG. 10B shows an exploded, enlarged detailed view of a part of the connector and combined access device and adapter shown in FIG. 10A.
Figure 10C:
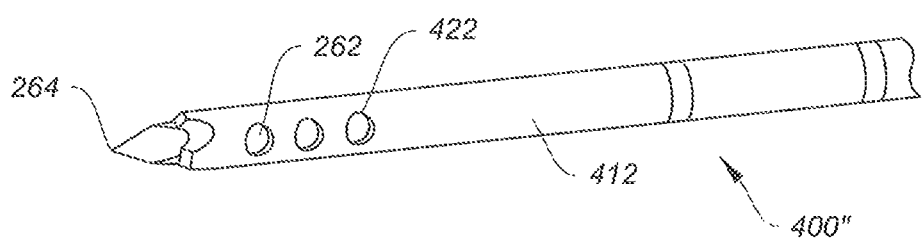
FIG. 10C shows an enlarged detailed view of a part of the connector and combined access device and adapter shown in FIG. 10A assembled together.

FIGS. 10A-10C show yet another exemplary connector and combined access device and adapter of the present disclosure. In this embodiment, the connector 250' is identical to the one previously shown and described in FIGS. 9A and 9B. The combined access device and adapter 400' is also similar to the one previously shown and described in FIGS. 9A and 9B, except that this embodiment includes additional fenestrations 422, as shown in greater detail in FIGS. 10B and 10C. When the central stem 262 is placed through the shaft 412 of the combined access device and adapter 400', the fenestrations 422 may be closed off, as can be seen in FIG. 10C showing the fully assembled product. Removal of the central stem 262 would therefore allow the fenestrations 422 to be open to either inject or extract material into or out of the patient, respectively, as desired.

Figure 11A:
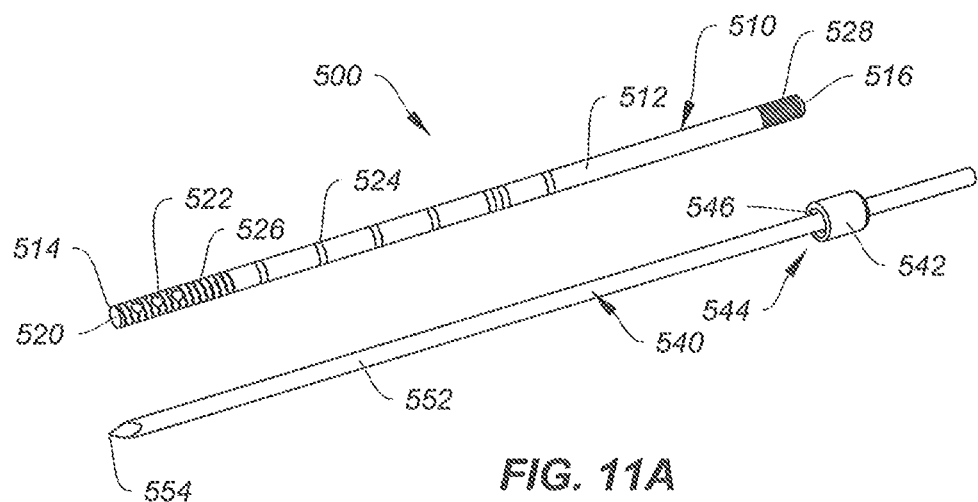
FIG. 11A shows an exploded view of an exemplary access device and adapter in accordance with yet another embodiment of the present disclosure.

FIG. 11A shows an exploded view of an exemplary access device and driving adapter system of the present disclosure. The system 500 may include an access device 510 that shares similar features to the access device 10 of FIGS. 1A and 1B, with like features sharing the same reference numeral following the prefix "5". Accordingly, the access device 510 of the system 500 may comprise a shaft 512, a first leading end 514, a second trailing end 516, a central channel 520, fenestrations 522, and etchings 524. In this embodiment, the first leading end 514 and second trailing end 516 may comprise threads 526, 528. Of course, as previously mentioned, the threads 526, 528 are optional and in other embodiments of the access device 510, these threads 526, 528 may be omitted. However, unlike access device 10, the access device 510 of the system 500 may have an open end 514.

The driving adapter 540 of the system 500 may comprise a main body 542 having a central opening 544 and internal threads 546 for threaded engagement with the second trailing end 516 of the access device 510. A central stem 552 having the general form of a stylus extends through the main body 542, as shown in FIG. 11A, and terminates into a sharp tip 554.

Figure 11B:
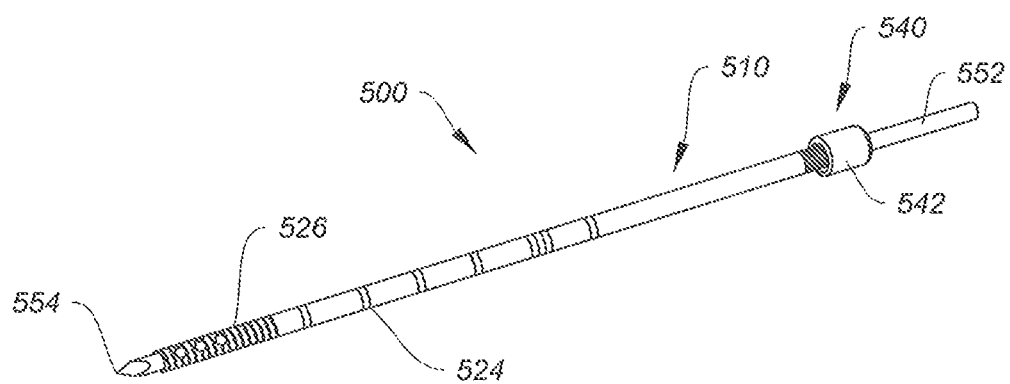
FIG. 11B shows a perspective view of the access device and adapter of FIG. 11A assembled together.

During assembly, the central body 542 may be threadedly engaged with the second trailing end 516 of the access device 510. The sharp tip 554 may extend through and protrude from the open end 514 of the access device 510, as shown in FIG. 11B. The combination of the driving adapter with the access device may be attached to another tool, such as a power tool, to be power driven into the patient's body. Upon removal of the driving adapter 540, the access device 510 may remain and the fenestrations 522 may be open to allow extraction or injection of material out of or into the patient. Other adapters 40 such as those described herein may then be connected to the access device 510 in a manner previously mentioned.

Figure 12A:
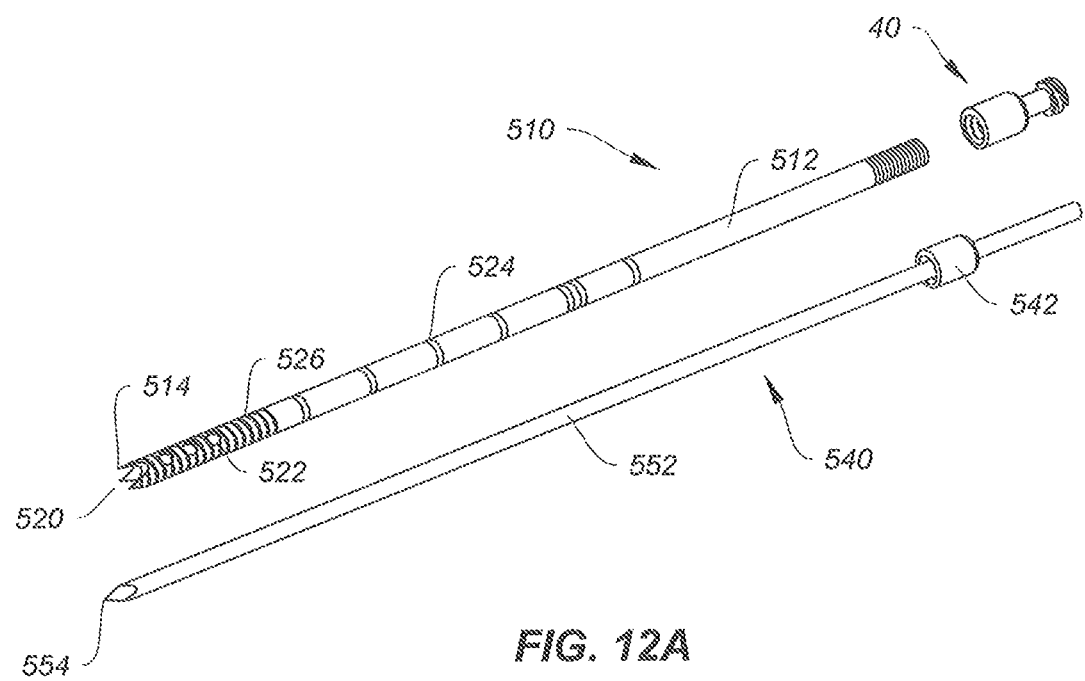
FIG. 12A shows an exploded view of an exemplary access device and adapter in accordance with another embodiment of the present disclosure.
Figure 12B:
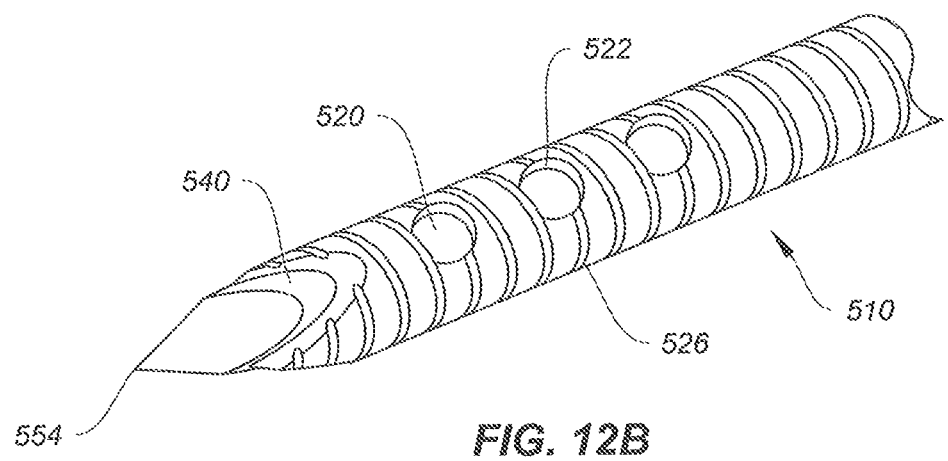
FIG. 12B shows an enlarged detailed view of a part of the access device and adapter of FIG. 12A assembled together.

FIG. 12A shows an exploded view of a system similar to system 500 just described, except that the open end 514 of the access device 510 may be shaped and have a configuration matching that of the sharp tip 554 of the driving adapter 540, as shown in detail in FIG. 12B. Additionally, the open end 514 may also include sharp edges, tips or projections for more secure engagement. While the driving adapter 540 is inside the access device 510, the fenestrations 522 may be closed off. It is understood, of course, that the access device 510 may be used with any of the adapters previously described, such as adapter 40 shown in FIG. 12A, either alone or along with driving adapter 540.

Figure 13A:
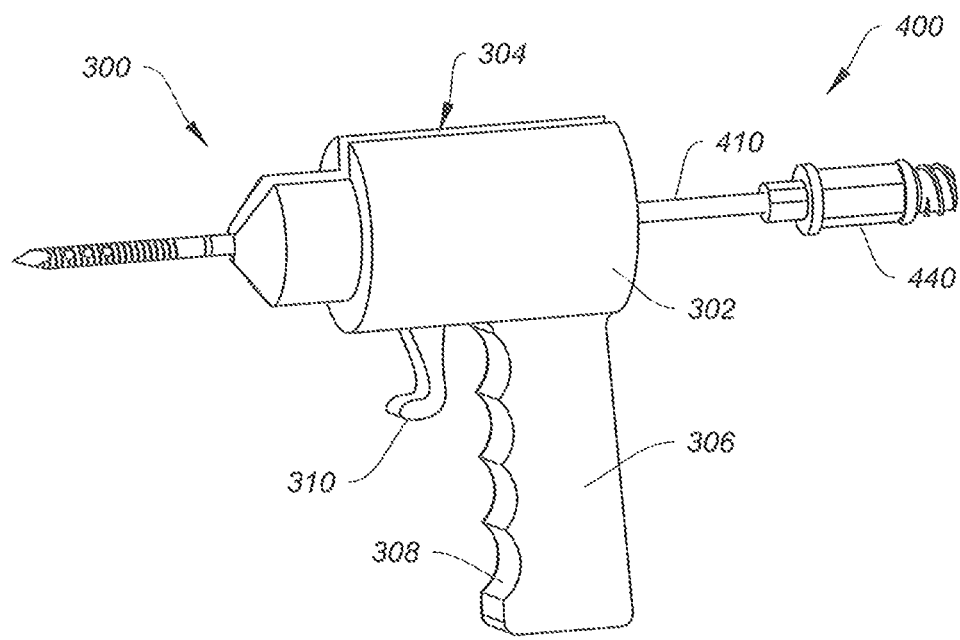
FIG. 13A shows an exemplary instrument system in accordance with an embodiment of the present disclosure.
Figure 13B:
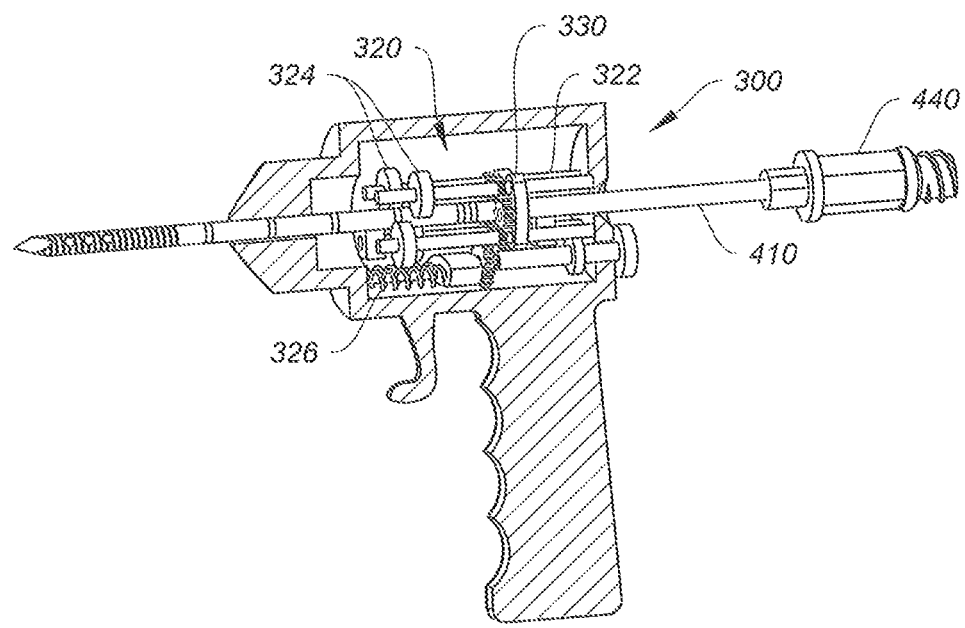
FIG. 13B shows a partial cutaway view of the instrument system shown in FIG. 13A.
Figure 13C:
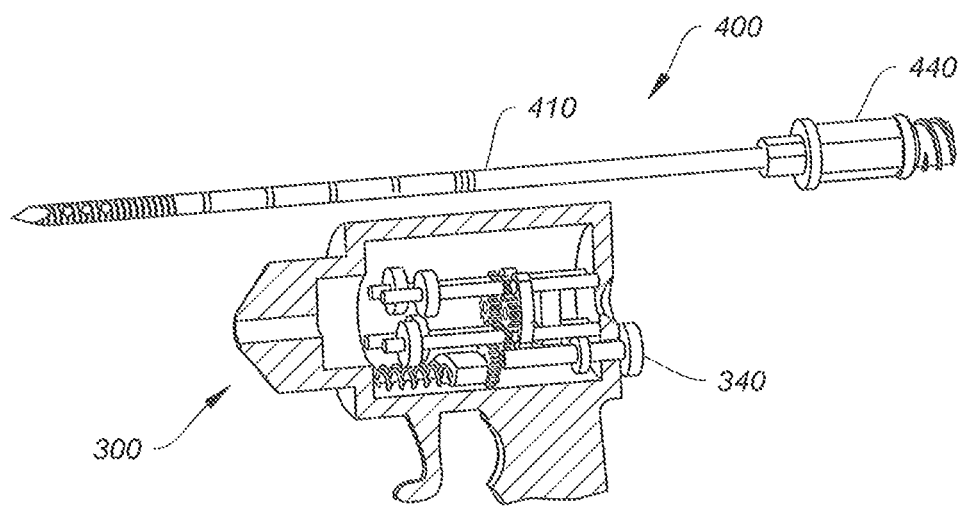
FIG. 13C shows an exploded view of the instrument system shown in FIG. 13A.
Figure 13D:
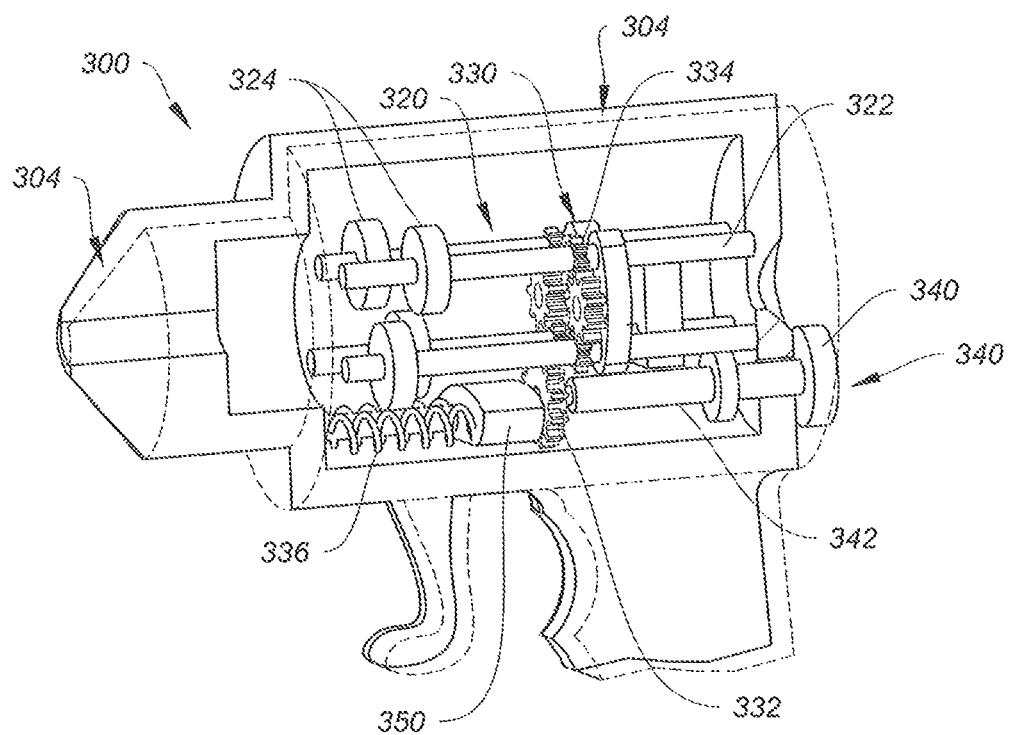
FIG. 13D shows a partial cutaway view of the power tool of the instrument system shown in FIG. 13A.

FIG. 13A shows an exemplary instrument system in accordance with an embodiment of the present disclosure. In this embodiment, the access device 10 with an adapter 40 may be directly drilled, without the need for a connector, into a site within a patient. As shown in FIGS. 13B-13D, the access device 10 may be securely held within a drill instrument 300. The drill instrument 300 may comprise a main body 302, a slot 304, a handle 306 having gripping notches 308, and a trigger 310 for actuating the drill instrument 300. The drill instrument 300 may be a cannulated drill that allows a user to remove the access device 10 from the drill 300 without having to pull the instrument 300 along the length of the access device 10. In other words, the drill instrument 300 may be configured so that it can be removed from the access device 10 by pulling it away, not along, the access device 10, as will be described in greater detail below.

FIGS. 13B-13D show various other views of the drill instrument 300 and illustrates how the access device 10 may be inserted and held. As shown in FIGS. 13B and 13D, the drill instrument 300 may include a capture mechanism 320 comprising driving rods 322 and driving discs 324. As shown, the drill instrument 300 may also include a gear mechanism 330 comprising a main gear 332, secondary gears 334, and springs 336 pushing a motor 350 against the main gear 332. A release mechanism 340 may be engaged by a release button 344 and comprises a shaft 342 connected to the main gear 332.

As shown in FIG. 13C, an access device 10 may be initially external to the drill instrument 300. The access device 10 is then moved down through slot 304 until it is held by driving discs 324 within the drill instrument 300, as shown in FIG. 13D. A user may then center the access device 10 within the drill instrument 300. The release mechanism 340 may be actuated and cause engagement of the motor 350 to main gear 332. The motor 350 may then be actuated by pulling the trigger 310. Removal of the drill instrument 300 may thus be achieved by pulling downwards and away from the access device 10, without disturbing the access device 10 or the adapter 40 once inserted into a patient's body, since the instrument 300 does not have to go over the second trailing end 16 of the access device 10 to be removed.

Figure 14:
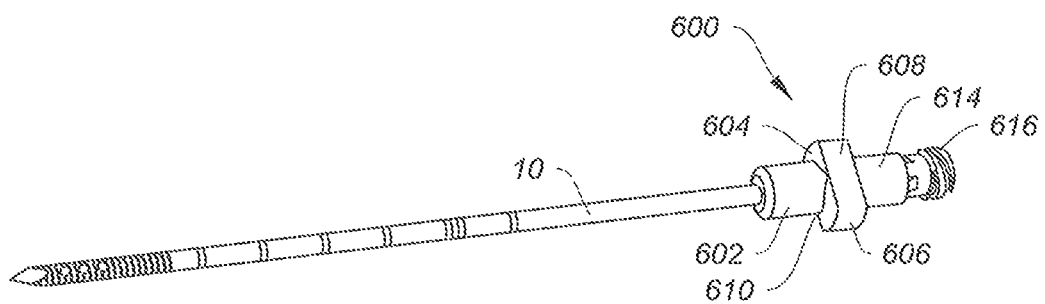
FIG. 14 shows another exemplary connector and access device in accordance with an embodiment of the present disclosure.

FIG. 14 shows another exemplary connector 600 and access device 10 in accordance with an embodiment of the present disclosure. As shown, the connector 600 may enclose an adapter (not shown in FIG. 14) in order to attach to access device 10. This allows a user to manipulate, rotated, drive forward, and pull the access device 10 as desired. The connector 600 may be a Hudson connector and comprise a main body 602 having a flange 604. The flange 604 may comprise round sidewalls 606 and flat sidewalls 608. The connector 600 may enclose an adapter within its central opening 610. A shaft 614 may extend from the flange 604 and terminate into a connector end 616. The connector end 616 may be a Luer lock, for example.

Figure 15:
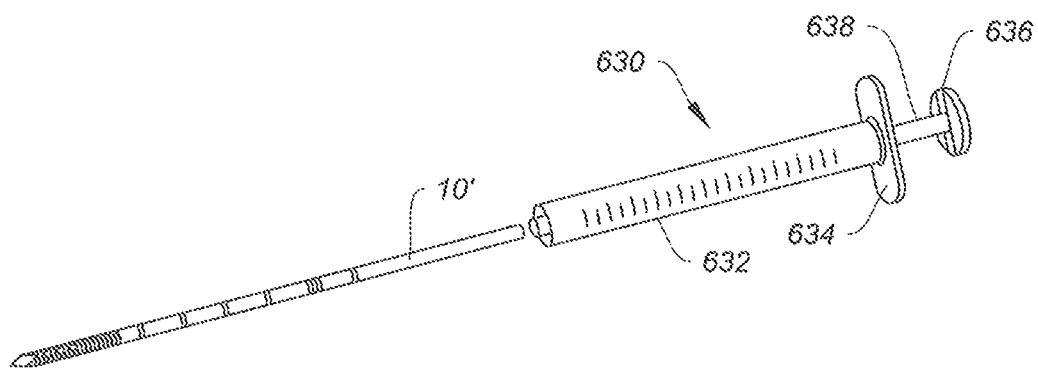
FIG. 15 shows an exemplary syringe and access device in accordance with an embodiment of the present disclosure.

FIG. 15 shows an exemplary syringe 630 and access device 10' in accordance with an embodiment of the present disclosure. As shown, a syringe 630 may be directly attached to the access device 10' and may comprise an outer shaft or body 632, a flange 634, an internal plunger 636, and internal shaft 636. The syringe 630 may be press fit over, or inside, the second trailing end 16 of the access device 10'.

The description of the invention is provided to enable any person skilled in the art to practice the various embodiments described herein. While the present disclosure has been particularly described with reference to the various figures and embodiments, it should be understood that these are for illustration purposes only and should not be taken as limiting the scope of the invention.

There may be many other ways to implement the invention. Various functions and elements described herein may be partitioned differently from those shown without departing from the spirit and scope of the invention. Various modifications to these embodiments will be readily apparent to those skilled in the art, and generic principles defined herein may be applied to other embodiments. Thus, many changes and modifications may be made to the invention, by one having ordinary skill in the art, without departing from the spirit and scope of the invention.

A reference to an element in the singular is not intended to mean "one and only one" unless specifically stated, but rather "one or more." The term "some" refers to one or more. Underlined and/or italicized headings and subheadings are used for convenience only, do not limit the invention, and are not referred to in connection with the interpretation of the description of the invention. All structural and functional equivalents to the elements of the various embodiments of the invention described throughout this disclosure that are known or later come to be known to those of ordinary skill in the art are expressly incorporated herein by reference and intended to be encompassed by the invention. Moreover, nothing disclosed herein is intended to be dedicated to the public regardless of whether such disclosure is explicitly recited in the above description.

What is claimed is:

1. An instrument system for providing access to a site within a body of a patient, said system comprising:
    a cannulated access device having a first leading end, a second trailing end and an elongate shaft extending therebetween;
    an adapter configured to attach to the second trailing end of the access device, the adapter comprising a main body, a central opening within the main body for receiving a portion of the second trailing end of the access device, and terminating into a connector end; and
    a connector configured to engage with the connector end of the adapter and provide a connection to another instrument, the connector including a main body defining an interior cavity and at least one wing member having an adapter engagement feature and a wing lever, the interior cavity sized to receive at least a portion of the main body of the adapter such that the main body of the connector is positionable over the main body of the adapter, wherein the adapter engagement feature extends from the main body of the connector in a first direction and the wing lever extends from the adapter engagement feature in a generally opposing second direction such that the wing lever is spaced from the main body of the connector, the wing lever depressible toward the main body of the connector to move the adapter engagement feature radially outward relative to the main body of the connector from a first position to a second position, the connector further including a central stem configured for insertion through the central opening of the adapter;
    wherein the interior cavity of the main body of the connector defines an interior geometry that mirrors an exterior geometry of the main body of the adapter to rotatably couple the connector to the adapter such that rotation of the connector drives a corresponding rotation of the adapter.

2. The system of claim 1, wherein the first leading end of the access device includes threads.

3. The system of claim 1, wherein the first leading end of the access device has a sharp tip.

4. The system of claim 1, wherein the second trailing end of the access device includes threads.

5. The system of claim 4, wherein the adapter is configured to attach to the second trailing end.

6. The system of claim 1, wherein the adapter comprises a clamp and is configured to provide a press-fit connection with the second trailing end of the access device.

7. The system of claim 6, wherein the clamp comprises a C-ring or a plurality of flanges separated by slots.

8. The system of claim 1, wherein the connector end comprises a Luer lock connection.

9. The system of claim 1, wherein the connector end comprises a Hudson connection.

10. The system of claim 1, wherein the access device comprises at least one fenestration.

11. The system of claim 1, wherein the access device comprises at least one visual marking.

12. The system of claim 1, wherein the connector is configured for connection to a drill instrument.

13. The system of claim 1, further comprising a drill instrument having a main body with a slot for receiving the shaft of the access device, a handle, and a trigger for actuating the drill instrument.

14. The system of claim 13, wherein the drill instrument comprises a catch mechanism comprising a plurality of driver discs.

15. The system of claim 13, wherein the drill instrument comprises a gear mechanism including a main gear, at least one secondary gear, a motor for driving the gears, and at least one spring biasing the gears against the motor.

16. The system of claim 13, wherein the drill instrument comprises a release mechanism including a release button extending from a shaft in connection with the main gear.

17. The system of claim 1, wherein the central stem has a sharp tip.

18. The system of claim 1, wherein the first leading end of the access device is open.

19. The system of claim 1, wherein the at least one wing member comprises a first wing member and a second wing member, each of the first and second wing members having an adapter engagement feature.

20. The system of claim 19, wherein the connector is configured to be removable from the adapter by pressing the first and second wing members inward towards the main body.

21. An instrument system for providing access to a site within a body of a patient, said system comprising:
a cannulated access device having a first leading end, a second trailing end and an elongate shaft extending therebetween;
an adapter configured to attach to the second trailing end of the access device, the adapter comprising a main body, a central opening within the main body for receiving a portion of the second trailing end of the access device, and terminating into a connector end; and
a connector configured to engage with the connector end of the adapter and provide a connection to another instrument, the connector including:
a main body defining an interior cavity, the main body of the connector being slideable over the main body of the adapter upon receipt of at least a portion of the main body of the adapter within the interior cavity;
a first wing member having a first adapter engagement feature and a first wing lever, the first adapter engagement feature being slideable over the main body of the adapter;
a second wing member having a second adapter engagement feature and a second wing lever, the second adapter engagement feature being slideable over the main body of the adapter;
wherein the first and second wing levers are depressible toward the main body of the connector to move the first and second adapter engagement features between an engaged position and a disengaged position; and
a central stem configured for insertion through the central opening of the adapter.

22. An instrument system for providing access to a site within a body of a patient, said system comprising:
a cannulated access device having a first leading end, a second trailing end and an elongate shaft extending therebetween;
an adapter configured to attach to the second trailing end of the access device, the adapter comprising a main body, a central opening within the main body for receiving a portion of the second trailing end of the access device, and terminating into a connector end; and
a connector configured to engage with the connector end of the adapter and provide a connection to another instrument, the connector including a main body defining an interior cavity and at least one wing member having an adapter engagement feature and a wing lever, the interior cavity sized to receive at least a portion of the main body of the adapter such that the main body of the connector is positionable over the main body of the adapter, wherein the adapter engagement feature extends in a first direction and the wing lever extends in a second direction generally opposite to the first direction, and wherein the wing lever is depressible toward the main body of the connector to move the adapter engagement feature from a first position to a second position, the connector further including a central stem having a length sufficient to extend through the central opening of the adapter and into the elongate shaft of the cannulated access device when the connector is engaged with the connector end of the adapter.

23. The instrument system of claim 22, wherein the wing lever is formed integral with the adapter engagement feature.

* * * * *